United States Patent
Nosaka et al.

(10) Patent No.: US 10,383,838 B2
(45) Date of Patent: *Aug. 20, 2019

(54) CONCENTRATED LIQUID DIET

(71) Applicant: The Nisshin OilliO Group, Ltd., Yokosuka-shi (JP)

(72) Inventors: Naohisa Nosaka, Yokosuka (JP); Katsuhiko Ooyama, Yokosuka (JP); Keiichi Kojima, Yokosuka (JP); Yoshie Suzuki, Yokosuka (JP)

(73) Assignee: The Nisshin OilliO Group, Ltd., Yokosuka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,405

(22) Filed: May 15, 2018

(65) Prior Publication Data
US 2018/0256531 A1 Sep. 13, 2018

Related U.S. Application Data

(60) Continuation of application No. 15/892,945, filed on Feb. 9, 2018, now Pat. No. 10,285,965, which is a division of application No. 13/091,853, filed on Apr. 21, 2011, now Pat. No. 9,907,774, which is a continuation of application No. PCT/JP2009/005656, filed on Oct. 27, 2009.

(30) Foreign Application Priority Data

Nov. 6, 2008 (JP) ................................ 2008-285832
May 13, 2009 (JP) ................................ 2009-116959

(51) Int. Cl.
*A61K 31/23* (2006.01)
*A23L 33/00* (2016.01)
*A23L 33/12* (2016.01)

(52) U.S. Cl.
CPC .............. *A61K 31/23* (2013.01); *A23L 33/12* (2016.08); *A23L 33/30* (2016.08); *A23V 2002/00* (2013.01)

(58) Field of Classification Search
USPC ............. 426/607, 612, 601, 801, 606, 330.6
See application file for complete search history.

(56) References Cited

U.S. PATENT DOCUMENTS

| | | | |
|---|---|---|---|
| 3,658,555 A | 4/1972 | Menz et al. | |
| 4,888,196 A | 12/1989 | Ehrman et al. | |
| 5,288,512 A | 2/1994 | Seiden | |
| 5,552,174 A | 9/1996 | Wheeler et al. | |
| 6,130,244 A | 10/2000 | DeMichele et al. | |
| 7,241,468 B2 | 7/2007 | Naber et al. | |
| 2004/0005368 A1 | 1/2004 | Mann et al. | |
| 2004/0142018 A1 | 7/2004 | Takeuchi et al. | |
| 2006/0167094 A1 | 7/2006 | Fleming et al. | |
| 2008/0311100 A1 | 12/2008 | Manissier et al. | |
| 2009/0247625 A1 | 10/2009 | Nakai et al. | |
| 2011/0081424 A1 | 4/2011 | Sliwinski et al. | |

FOREIGN PATENT DOCUMENTS

| | | |
|---|---|---|
| EP | 0843972 A1 | 5/1998 |
| JP | 1243970 A | 9/1989 |
| JP | 2001-245633 A | 9/2001 |
| JP | 2006-117557 A | 5/2006 |
| JP | 2006-136318 A | 6/2006 |
| KR | 2004-016985 A | 2/2004 |
| TW | 2008-12569 A | 3/2008 |
| WO | 97/07690 A2 | 3/1997 |
| WO | 2004/000044 A1 | 12/2003 |
| WO | 2007/000529 A2 | 1/2007 |
| WO | 2007/080149 A2 | 7/2007 |
| WO | 2007/115282 A2 | 10/2007 |
| WO | 2007/132714 A1 | 11/2007 |

OTHER PUBLICATIONS

International Search Report issued in related International Patent Application No. PCT/JP2009/005656 dated Jan. 19, 2010.
Extended European Search Report issued in related European Patent Application No. 09824548.3 dated Feb. 6, 2014.
Office Action issued in related Taiwanese Patent Application No. 098137478 dated Feb. 6, 2014.
Van Hoogdalem et al., "Absorption enhancement of rectally infused cefoxitin sodium by medium-chain fatty acids in conscious rats: concentration-effect relationship," Pharmaceutical Research, 5: 453-456 (1988).
"PEPTAMEN 1.5 product details," Nestle Health Science, https://www.nestlehealthscience.us/brands/peptamen/peptame1-5> 3 pages, retrieved Mar. 9, 2016.
"Nu-Chek Prep, Inc., the Home of Fine Lipid Organics" 2007 catalgoue, 2 pages, retrieved Mar. 9, 2016.
Bach et al., "The usefulness of dietary medium-chain triglycerides in body weight control: fact or fancy?" Journal of Lipid Research, 37: 708-726 (1996).
Heydinger et al., "Medium Chain Triacylglycerols," Journal of Food Lipids, 3: 251-257 (1996).
Opposition issued in related European Patent Application No. 09824548.3 dated Mar. 14, 2016.

(Continued)

*Primary Examiner* — Tamra L. Dicus
(74) *Attorney, Agent, or Firm* — Morgan, Lewis & Bockius LLP

(57) ABSTRACT

The concentrated liquid diet disclosed is a concentrated liquid diet having a total amount of a medium-chain fatty acid having 8 carbon atoms and a medium-chain fatty acid having 10 carbon atoms included as constitutive fatty acids of a triglyceride being 2.5 to 8.0 g per 100 kcal of the energy of the concentrated liquid diet, the concentrated liquid diet having in the total mass of the medium-chain fatty acid having 8 carbon atoms and the medium-chain fatty acid having 10 carbon atoms the rate of the medium-chain fatty acid having 10 carbon atoms being no less than 60% by mass, and the rate of the medium-chain fatty acid having 8 carbon atoms being no greater than 40% by mass.

9 Claims, No Drawings

(56) References Cited

OTHER PUBLICATIONS

"Regulation (EU) No. 1169/2011 of the European Parliament and of the Council of Oct. 25, 2011," Official Journal of the European Union, 1-46, Nov. 22, 2011.
Office Action issued in related Korean Patent Application No. 10-2011-7011588 dated May 12, 2016.
Oral Proceedings issued in European Patent Application No. 09824548.3 dated Sep. 13, 2017.
"Alphabetical List of Compounds," Biochemical and Reagents for Life Science Research, SIGMA (1999).
"Nestle Peptamen 1.5: Complete High Calorie Elemental Diet," Nestle Clinical Nutrition (2001).
Bezard et al., "The Component Triglycerides of Palm-Kernal Oil," Lipids, 6: 630-634 (1971).
Zambiazi et al., "Fatty Acid Compositions of Vegetable Oils and Fats," B.CEPPA, Curitiba, 25: 111-120 (2007).
Bezard et al., "Triglyceride Composition of Coconut Oil," Journal of the American Oil Chemists' Society, 48: 134-139 (1970).
Calories in L-Carnitine (500mg), Calories and Nutrition Facts (2018).
Grounds of Appeal issued in related European Patent Application No. 09824548.3 dated Apr. 17, 2018.

CONCENTRATED LIQUID DIET

CROSS RELATED APPLICATIONS

This application claims benefit of U.S. application Ser. No. 15/892,945, filed Feb. 9, 2018, which claims benefit of U.S.application Ser. No. 13/091,853, filed Apr. 21, 2011, which claims benefit of PCT/JP2009/005656, filed Oct. 27, 2009, which claims benefit of JP2008285832, filed Nov. 6, 2008 and JP2009116959, filed May 13, 2009.

TECHNICAL FIELD

The present invention relates to a concentrated liquid diet. More particularly, the present invention relates to a concentrated liquid diet that is less likely to strain the stomach irrespective of containing a fat and oil as a principal energy source.

BACKGROUND ART

Concentrated liquid diets are used for nutritional support of elderly people, hospitalized patients and the like. Therefore, concentrated liquid diets are required to contain nutrients such as proteins, lipids, glucides and minerals blended with a good balance.

On the other hand, in the case of patients prior to and/or following an operation, an element composition that provides energy and proteins for repairing the damaged tissue to be promptly supplied is desired rather than the nutrition balance. Nutrients available as an energy source include proteins, lipids and glucides, and proteins are readily utilized for energy subsequent to glucides. Thus, as a result of consumption of proteins as an energy source, deficiency in proteins may be caused which are required as components for the bodily reparative tissue, or required in an immunoreaction. As a fatty acid having an effect of suppressing consumption of such proteins as an energy source, medium-chain fatty acids have been known. In addition, medium-chain fatty acids are quickly absorbed in the gastrointestinal tract, and degraded extremely fast in the liver and energized. Therefore, it is believed that the energy can be supplied efficiently without allowing proteins to be excessively consumed as an energy source, if a large amount of a medium-chain fatty acid can be blended in a liquid diet.

However, fats and oils ingested in a large amount may, in general, lead to strain on the stomach such as heavy stomach feeling, and the medium-chain fatty acids may also induce discomfort of the upper abdomen such as heavy stomach feeling and irritation of stomach when a large amount is ingested at a single time. Therefore, a medium-chain fatty acid is not blended in a large amount. In fact, although a liquid diet blended with a triglyceride including a medium-chain fatty acid as a constitutive fatty acid was reported (Patent Documents 1 and 2), the amount blended therein is limited to a low level. Thus, development of a concentrated liquid diet that contains a large amount of a medium-chain fatty acid, and that is less likely to strain the stomach has been desired.

Patent Document 1: Japanese Unexamined Patent Application, Publication No. 2001-245633
Patent Document 2: Japanese Unexamined Patent Application, Publication No. 2006-136318

DISCLOSURE OF THE INVENTION

Problems to be Solved by the Invention

The present invention was made in view of the foregoing circumstances, and an object of the present invention is to provide a concentrated liquid diet that contains a large amount of medium-chain fatty acids capable of efficiently supplying energy, and that is less likely to strain the stomach.

Means for Solving the Problems

The present inventor thoroughly investigated in order to solve the aforementioned problems, and consequently found that selecting n-octanoic acid that is a fatty acid having 8 carbon atoms and n-decanoic acid that is a fatty acid having 10 carbon atoms as medium-chain fatty acids that constitute the triglyceride, and including n-decanoic acid at a rate greater than n-octanoic acid enable medium-chain fatty acids having favorable energy efficiency to be ingested in a large amount without significantly straining the stomach. Accordingly, the present invention was accomplished. More specifically, the present invention provides as in the following.

A first aspect of the present invention provides a concentrated liquid diet having a total amount of a medium-chain fatty acid having 8 carbon atoms and a medium-chain fatty acid having 10 carbon atoms included as constitutive fatty acids of a triglyceride being 2.5 to 8.0 g per 100 kcal of the energy of the concentrated liquid diet, the concentrated liquid diet having in the total mass of the medium-chain fatty acid having 8 carbon atoms and the medium-chain fatty acid having 10 carbon atoms a rate of the medium-chain fatty acid having 10 carbon atoms being no less than 60% by mass, and a rate of the medium-chain fatty acid having 8 carbon atoms being no greater than 40% by mass.

A second aspect of the present invention provides the concentrated liquid diet according to the first aspect, in which the total amount of the medium-chain fatty acid having 8 carbon atoms and the medium-chain fatty acid having 10 carbon atoms included as constitutive fatty acids of the triglyceride is 2.5 to 6 g per 100 kcal of the energy of the concentrated liquid diet.

A third aspect of the present invention provides the concentrated liquid diet according to the first or second aspect, in which, in the total mass of the medium-chain fatty acid having 8 carbon atoms and the medium-chain fatty acid having 10 carbon atoms, the rate of the medium-chain fatty acid having 10 carbon atoms is 75 to 95% by mass, and the rate of the medium-chain fatty acid having 8 carbon atoms is 5 to 25% by mass.

A fourth aspect of the present invention provides the concentrated liquid diet according to any one of the first to third aspects, in which the triglyceride is included in an amount of 2.6 to 10 g per 100 kcal of the energy of the concentrated liquid diet.

Effects of the Invention

According to the present invention, n-octanoic acid that is a fatty acid having 8 carbon atoms and n-decanoic acid that is a fatty acid having 10 carbon atoms are selected as medium-chain fatty acids that constitute a triglyceride, and n-decanoic acid is included at a rate greater than n-octanoic acid; therefore, ingestion of a large amount of medium-chain fatty acids having favorable energy efficiency is enabled without significantly straining the stomach.

Also, in the case of patients prior to and/or following an operation, it is necessary to promptly supply energy and proteins for repairing the damaged tissue. Thus, according to the present invention, since medium-chain fatty acids that are quickly absorbed in the gastrointestinal tract, and degraded extremely fast in the liver and energized are contained in a large amount, the energy can be efficiency supplied. Therefore, utilization in repairing the tissue in a body is enabled without excessively consuming the proteins as an energy source, whereby recovery in an early stage can be expected.

PREFERRED MODE FOR CARRYING OUT THE INVENTION

Hereinafter, embodiments of the present invention will be explained in detail.

The concentrated liquid diet of the present invention is characterized by being a concentrated liquid diet having a total amount of a medium-chain fatty acid having 8 carbon atoms and a medium-chain fatty acid having 10 carbon atoms included as constitutive fatty acids of a triglyceride being 2.5 to 8.0 g per 100 kcal of the energy of the concentrated liquid diet, the concentrated liquid diet having in the total mass of the medium-chain fatty acid having 8 carbon atoms and the medium-chain fatty acid having 10 carbon atoms the rate of the medium-chain fatty acid having 10 carbon atoms being no less than 60% by mass, and the rate of the medium-chain fatty acid having 8 carbon atoms being no greater than 40% by mass.

According to the concentrated liquid diet of the present invention, the total amount of a medium-chain fatty acid having 8 carbon atoms and a medium-chain fatty acid having 10 carbon atoms included as constitutive fatty acids of the triglyceride is set to be 2.5 to 8.0 g per 100 kcal of the energy of the concentrated liquid diet for efficiently supply an energy. Moreover, in order to reduce strain on the stomach due to ingestion of the triglyceride in a large amount at a single time, in the total mass of the medium-chain fatty acid having 8 carbon atoms and the medium-chain fatty acid having 10 carbon atoms the rate of the medium-chain fatty acid having 10 carbon atoms is set to be no less than 60% by mass, and the rate of the medium-chain fatty acid having 8 carbon atoms in the same total mass is set to be no greater than 40% by mass.

(Concentrated Liquid Diet)

The term "concentrated liquid diet" herein means an enteral formula or a parenteral formula having at least 0.8 kcal/g (ml) of energy used for supplying necessary nutrition, and used as a food or a medical drug. The concentrated liquid diet in the present invention may be in the form of a liquid, gel, etc., upon ingestion but may be in the form of powder before ingestion. In the concentrated liquid diet of the present invention, it is not necessary to include well-balanced nutrients such as proteins, lipids, glucides, minerals and vitamins, and rather may contain lipids as a main calorie source. Also, the concentrated liquid diet of the present invention may be eaten as a soup prepared by blending an ingredient such as pumpkin, corn, or onion (paste, ground product, powder, or the like). Furthermore, a food with a low salt content and high energy can be produced by setting the blend ratio so as to give a salt content per meal being no greater than 50% by mass of that provided by similar types of foods. For example, in the case of a soup, a soup having a low salt and protein contents and high energy can be produced by blending such that the amount of a dietary salt added is reduced to make the amount of salt per meal of 0.4 g, and dextrin is included in place of proteinous food ingredients.

The concentrated liquid diet of the present invention is characterized in that the total amount of a medium-chain fatty acid having 8 carbon atoms and a medium-chain fatty acid having 10 carbon atoms included as constitutive fatty acids of the triglyceride is 2.5 to 8.0 g, and preferably 2.5 to 6 g per 100 kcal of the energy of the concentrated liquid diet. Since the concentrated liquid diet is often used for patients who must ingest necessary nutritional components while securing the energy, the blend ratio of the nutritional components is preferably represented by the amount per 100 kcal of the energy of the concentrated liquid diet. When the amount falls within the above range, even in the case of patients prior to and/or following an operation who must be promptly supplied with an energy and proteins, necessary energy can be efficiently supplied from a medium-chain fatty acid having 8 carbon atoms and a medium-chain fatty acid having 10 carbon atoms; therefore, the proteins can be utilized for repairing the damaged tissue without being consumed as energy, whereby recovery in an early stage can be expected. It is to be noted that the energy per gram of lipids is 9 kcal.

Although the concentrated liquid diet of the present invention contains a triglyceride, the triglyceride may be either a single acid triglyceride including only a medium-chain fatty acid having 8 or 10 carbon atoms as a constitutive fatty acid, or a mixed acid triglyceride including medium-chain fatty acids having 8 and 10 carbon atoms as a constitutive fatty acid. In the case of the mixed acid triglyceride, binding position of each medium-chain fatty acid to glycerin is not particularly limited. Also, in the case of the mixed acid triglyceride, a part of the constitutive fatty acids may include a medium-chain fatty acid other than those having 8 or 10 carbon atoms, and a long-chain fatty acid may be included.

In addition, the concentrated liquid diet of the present invention is characterized in that in the total mass of the medium-chain fatty acid having 8 carbon atoms and the medium-chain fatty acid having 10 carbon atoms included as constitutive fatty acids of the triglyceride the rate of the medium-chain fatty acid having 10 carbon atoms is no less than 60% by mass, and the rate of the medium-chain fatty acid having 8 carbon atoms in the same total mass is no greater than 40% by mass. In other words, the rate of the medium-chain fatty acid having 10 carbon atoms is 60 to 100% by mass, and the rate of the medium-chain fatty acid having 8 carbon atoms is 0 to 40% by mass. Preferably, the rate of the medium-chain fatty acid having 10 carbon atoms is 60 to 95% by mass, and the rate of the medium-chain fatty acid having 8 carbon atoms is 5 to 40% by mass. More preferably, the rate of the medium-chain fatty acid having 10 carbon atoms is 75 to 95% by mass, and the rate of the medium-chain fatty acid having 8 carbon atoms is 5 to 25% by mass. Most preferably, the rate of the medium-chain fatty acid having 10 carbon atoms is 80 to 95% by mass, and the rate of the medium-chain fatty acid having 8 carbon atoms is 5 to 20% by mass. When the rate falls within the above range, strain on the stomach such as heavy stomach feeling and irritation is limited even if ingested in a large amount at a single time, and favorable flow performance of the triglyceride is attained leading to superior handlability. It is to be noted that the rate of the medium-chain fatty acid having 10 carbon atoms may be 100% by mass; however, since n-decanoic acid has a melting point of 31° C. and is thus easily hardened, a fatty acid not having 10 carbon atoms such as, for example, n-octanoic acid that is a saturated fatty acid having 8 carbon atoms, is preferably included in the range described above in order to achieve even superior handlability.

In the concentrated liquid diet of the present invention, the medium-chain fatty acids each having 8 and 10 carbon atoms included as constitutive fatty acids of the triglyceride are preferably saturated fatty acids. For example, the saturated fatty acid having 8 carbon atoms is exemplified by n-octanoic acid, whereas the saturated fatty acid having 10 carbon atoms is exemplified by n-decanoic acid. The medium-chain fatty acid is quickly absorbed in the gastrointestinal tract and degraded extremely fast in the liver; therefore, the energy can be efficiency supplied by the concentrated liquid diet containing a large amount of the medium-chain fatty acid.

Although the method for producing the triglyceride is not particularly limited, for example, a triglyceride including a medium-chain fatty acid having 8 carbon atoms and a medium-chain fatty acid having 10 carbon atoms as constitutive fatty acids may be obtained by allowing an esterification reaction using a medium-chain fatty acid having 8 carbon atoms and a medium-chain fatty acid having 10 carbon atoms derived from coconut oil or palm kernel oil, and glycerin as raw materials. Conditions of the esterification reaction are not particularly limited, and the reaction may be allowed either under pressure in the absence of both a catalyst and a solvent, or using a catalyst and/or a solvent. Alternatively, the triglyceride including a medium-chain fatty acid having 8 carbon atoms and a medium-chain fatty acid having 10 carbon atoms as constitutive fatty acids may be obtained by squeezing and extracting oilseeds of a genetic recombinant plant as a raw material, or the triglyceride can be also produced using a medium-chain fatty acid having 8 carbon atoms and a medium-chain fatty acid having 10 carbon atoms obtained from an oilseed of a genetic recombinant plant as a raw material.

As a method for adjusting the rate of fatty acids constituting the triglyceride, for example, a method in which after a simple triglyceride consisting of n-octanoic acid that is a medium-chain fatty acid having 8 carbon atoms and a simple triglyceride consisting of n-decanoic acid that is a medium-chain fatty acid having 10 carbon atoms are produced, they are mixed to give a desired rate, or a method in which n-octanoic acid and n-decanoic acid are prepared at a desired rate beforehand and allowed to form ester bonds with glycerin, and the like may be exemplified.

As a method for verifying the rate of the medium-chain fatty acids each having 8 and 10 carbon atoms in the total mass of the medium-chain fatty acid having 8 carbon atoms and the medium-chain fatty acid having 10 carbon atoms included as the constitutive fatty acids of the triglyceride, for example, a method in which fatty acids constituting the triglyceride are subjected to methyl esterification, followed by a quantitative determination analysis carried out by gas chromatography may be exemplified.

In the concentrated liquid diet of the present invention, a fat and oil may be contained as a lipid in addition to the triglyceride used in the present invention, and for example, may include soybean oil, rapeseed oil, high-oleic rapeseed oil, corn oil, sesame oil, sesame salad oil, Japanese basil oil, linseed oil, peanut oil, high-linoleic safflower oil, high-oleic safflower oil, sunflower oil, high-oleic sunflower oil, mid oleic sunflower oil, cotton seed oil, grape seed oil, macadamia nut oil, hazelnut oil, pumpkin seed oil, walnut oil, camellia oil, tea seed oil, perils oil, borage oil, olive oil, rice oil, rice bran oil, wheat germ oil, palm oil, palm kernel oil, coconut oil, cacao butter, beef tallow, lard, chicken fat, milk fat, fish oil, seal oil, algal oil, fats and oils thereof prepared by lowering the saturation by bleeding, and mixed fats and oils of the same, hydrogenated fats and oils, fractionated fats and oils, interesterified fats and oils, and the like. It should be noted that the concentrated liquid diet as a whole preferably contains 2.6 to 10 g of the triglyceride per 100 kcal of the energy of the concentrated liquid diet in the present invention.

Also, in addition thereto, various types of nutritional components such as proteins, glucides, vitamins and minerals, and food additives such as a stabilizer, an emulsifying agent and a flavor may be included in the concentrated liquid diet of the present invention to meet the object in the range not to impair the effects of the present invention. Although the protein is not particularly limited, milk proteins, soybean proteins, egg yolk proteins, or degradation products of the same may be included. In addition, also the glucide is not particularly limited, and glucose, sucrose, fructose, dextrin, starch, or processed products of the same may be included. Further, as ingredients of the concentrated liquid diet, paste, ground products, powdered and the like of pumpkin, corn, onion, etc., may be used.

The amount of concentrated liquid diet of the present invention administered is predetermined appropriately depending on the symptom of the subject when used as a medical drug, whereas the amount is not particularly limited when used as a food, and may be predetermined similarly to common foods.

The form of packaging the concentrated liquid diet of the present invention is not particularly limited, and may be arbitrarily selected to meet the object as far as it is generally used for concentrated liquid diets. For example, can, paper vessel, aluminum laminated pouch, bottle, and the like may be exemplified. It is to be noted that the concentrated liquid diet of the present invention is subjected to a high-temperature sterilization treatment, followed by packing into a vessel in a sterilized clean room or the like, alternatively after packed in vessel once, the concentrated liquid diet of the present invention may be subjected to retort sterilization.

EXAMPLES

Next, the present invention will be explained in more detail by way of several examples, but the present invention is not limited thereto.

[Production of Triglyceride]

Production Example 1

Method for Producing Glycerol Tri-n-Octanoate n-Octanoic acid (manufactured by Miyoshi Oil & Fat Co., Ltd.) in an amount of 570 g and 110 g of glycerin (manufactured by Miyoshi Oil & Fat Co., Ltd.) were mixed, and a reaction was allowed while dehydrating at 240° C. for 24 hrs to obtain glycerol tri-n-octanoate.

Production Example 2

Method for Producing Glycerol Tri-n-Decanoate n-Decanoic acid (manufactured by Miyoshi Oil & Fat Co., Ltd.) in an amount of 850 g and 140 g of glycerin (manufactured by Miyoshi Oil & Fat Co., Ltd.) were mixed, and a reaction was allowed while dehydrating at 240° C. for 24 hrs to obtain glycerol tri-n-decanoate.

Reference Examples

First, results of investigation in animals are shown as Reference Examples.

[Test for Investigating Irritation of Gastric Mucosa in Rat]

Rats were administered with emulsions for tests having varying blend ratios of glycerol tri-n-octanoate and glycerol tri-n-decanoate to investigate the relationship between the constitutive fatty acids of the triglyceride and irritation of gastric mucosa.

[Preparation of Emulsion for Tests]

Reference Example 1

To water at 70° C. were added casein, dextrin and an emulsifying agent, and mixed with a disperser. Thereto was added a mixture of the glycerol tri-n-octanoate produced by the method of Production Example 1, and the glycerol tri-n-decanoate produced by the method of Production Example 2 at a ratio of 40:60, followed by emulsification with ultrasound to obtain an emulsion for tests. The blend ratios are shown in Table 1.

TABLE 1

Composition of Emulsions for Tests

|  | Reference Example 1 | Reference Example 2 | Reference Example 3 | Comparative Reference Example 1 |
|---|---|---|---|---|
| n-Octanoic Acid:n-Decanoic Acid in Triglyceride | 40:60 | 20:80 | 0:100 | 60:40 |

| Component | Composition (parts by mass) | | | |
|---|---|---|---|---|
| Triglyceride | 50 | 50 | 50 | 50 |
| Casein | 5 | 5 | 5 | 5 |
| Dextrin | 5 | 5 | 5 | 5 |
| Emulsifying agent | 1 | 1 | 1 | 1 |
| Water | 39 | 39 | 39 | 39 |

Reference Example 2

An emulsion for tests was obtained in a similar manner to Reference Example 1 except that the glycerol tri-n-octanoate produced by the method of Production Example 1, and the glycerol tri-n-decanoate produced by the method of Production Example 2 mixed at a ratio of 20:80 was used as the triglyceride.

Reference Example 3

An emulsion for tests was obtained in a similar manner to Reference Example 1 except that the glycerol tri-n-decanoate produced by the method of Production Example 2 was used as the triglyceride.

Comparative Reference Example 1

An emulsion for tests was obtained in a similar manner to Reference Example 1 except that the glycerol tri-n-octanoate produced by the method of Production Example 1, and the glycerol tri-n-decanoate produced by the method of Production Example 2 mixed at a ratio of 60:40 was used as the triglyceride.

[Test Method 1] Reference Examples 1 to 3, and Comparative Reference Example 1

Five male 10-week old Wistar rats having a body weight of about 200 g (Japan SLC, Inc.) as one test group were subjected to tests by administration. Each emulsion for tests (Reference Examples 1 to 3, and Comparative Reference Example 1) prepared by the aforementioned method was orally administered to the rat after fasting for 18 hrs. The amount of the triglyceride administered was 2 g per kg of body weight. After placing at rest for 1 hour following the administration, an incision was made in the abdomen under anesthesia, and the stomach was extirpated. Then, the extirpated stomach was incised along the greater curvature, and the gastric mucosa was washed with physiological saline and visually observed, with use of a loupe as needed. It should be noted that evaluation in connection with the irritation of gastric mucosa was made in accordance with a method described in a document (Yakugaku Zasshi 89 (8): 1114-1118, 1978). The criteria of evaluation are shown below.

[Criteria of Evaluation]

(−): Nine or less areas of patchy redness found.

(+): Ten or more areas of patchy redness found, and sum total of each length of erosion being no greater than 2 mm.

(++): Twenty or more areas of patchy redness found, and sum total of each length of erosion being no greater than 10 mm.

(+++): Sum total of each length of ulcer, or erosion being no less than 10 mm.

It is to be noted that when evaluation was made as (−), the number of areas of patchy redness was counted.

[Test Method 2] Positive Control Group

Similar method to Test Method 1 was carried out except that ethanol was administered.

[Test Method 3] Negative Control Group

A similar method to the Test Method 1 was carried out except that physiological saline was administered.

TABLE 2

Test for Investigating Irritation of Gastric Mucosa of Rat

|  | Positive Control Group | Comparative Control Group Comparative Reference Example 1 | Test group | | | Negative Control Group |
|---|---|---|---|---|---|---|
|  |  |  | Reference Example 1 | Reference Example 2 | Reference Example 3 |  |
| Dose (g/kg · BW) | 2 | 2 | 2 | 2 | 2 | 2 |
| Irritation of gastric mucosa | (+++) | (−) | (−) | (−) | (−) | (−) |
| Number of areas of patchy redness | — | 5.6 ± 0.5 | 4.0 ± 0.6 * | 2.2 ± 0.5 * | 2.6 ± 0.7 * | 2.0 ± 0.5 * |

Mean ± SD
* Significantly different as compared with Comparative Reference Example 1 ($P < 0.05$)

Results of evaluation of irritation of gastric mucosa and the number of areas of patchy redness of the rats orally administered with each emulsion for tests are shown in Table 2. Erosion or ulceration of the gastric mucosa was not found in any of the groups orally administered with the emulsion for tests of the present invention (Reference Examples 1 to 3), and more than nine areas of patchy redness was not found. Thus, irritation of gastric mucosa was evaluated as negative (−) for these groups. Therefore, it was ascertained that even if the medium-chain fatty acid is administered in an amount corresponding to about 120 g per 60 kg of the body weight of a human, gastric mucosa would not be significantly affected.

When compared in more detail, as the rate of n-decanoic acid that is a medium-chain fatty acid having 10 carbon atoms increased, the number of areas of patchy redness decreased. Reference Examples 1 to 3 exhibited significantly lower values as compared with Comparative Reference Example 1, and particularly, Reference Examples 2 and 3 exhibited the number of redness equivalent to the Negative Control Group in which physiological saline was administered.

From these results, it was revealed that irritation of gastric mucosa can be reduced by increasing the rate of n-decanoic acid that is a medium-chain fatty acid having 10 carbon atoms than n-octanoic acid that is a medium-chain fatty acid having 8 carbon atoms as the constitutive fatty acid of the triglyceride blended in the emulsion for tests.

EXAMPLES

[Test for Investigating Discomfort of the Upper Abdomen in Human]

Concentrated liquid diets having varying rates of glycerol tri-n-octanoate and glycerol tri-n-decanoate were administered to human, and thus a relationship between the constitutive fatty acids of the triglyceride and the influence on perception of upper abdominal sensation was investigated.

[Preparation of Concentrated Liquid Diet]

Preparation Example 1

Liquid Diets for Blend 1 to 3

To water at 70° C. were added casein, whole milk powder, white superior soft sugar, dextrin and an emulsifying agent in this order, and mixed with a disperser. To the mixture was added the glycerol tri-n-octanoate produced by the method of Production Example 1 while stirring with a homomixer, whereby liquid diets for blend 1 to 3 were obtained. The blend ratio is shown in Table 3.

Preparation Example 2

Liquid Diets for Blend 4 to 6

To water at 70° C. were added casein, whole milk powder, white superior soft sugar, dextrin and an emulsifying agent in this order, and mixed with a disperser. To the mixture was added the glycerol tri-n-decanoate produced by the method of Production Example 2 while stirring with a homomixer, whereby liquid diets for blend 4 to 6 were obtained. The blend ratio is shown in Table 3.

TABLE 3

| | Composition of liquid diet for blend | | | | | |
|---|---|---|---|---|---|---|
| | 1 | 2 | 3 | 4 | 5 | 6 |
| n-Octanoic Acid:n-Decanoic Acid in Triglyceride | 100:0 | 100:0 | 100:0 | 0:100 | 0:100 | 0:100 |
| Component | Blend (g) | | | | | |
| Triglyceride | 98.91 | 197.64 | 256.71 | 197.82 | 395.29 | 236.96 |
| Casein | 65.94 | 65.88 | 57.05 | 131.88 | 131.76 | 52.66 |
| Whole milk powder | 65.94 | 65.88 | 57.05 | 131.88 | 131.76 | 52.66 |
| White superior soft sugar | 32.97 | 32.94 | 28.52 | 65.94 | 65.88 | 26.33 |
| Dextrin | 461.58 | 230.58 | 0.00 | 923.17 | 461.17 | 0.00 |
| Emulsifying agent | 2.97 | 5.93 | 7.70 | 5.93 | 11.86 | 7.11 |
| Water | 2571.69 | 2701.14 | 2452.98 | 5143.37 | 5402.28 | 2264.29 |
| Total | 3300.00 | 3300.00 | 2860.00 | 6600.00 | 6600.00 | 2640.00 |

Example 1

The liquid diet for blend 1 prepared by the method of Preparation Example 1 in an amount of 600 g, and the liquid diet for blend 4 prepared by the method of Preparation Example 2 in an amount of 900 g were mixed to obtain a concentrated liquid diet. After thus obtained concentrated liquid diet of each 100 g was packaged by sealing into a retort vessel, retort sterilization (121° C., for 15 min) was carried out, and divided so as to be ingestible for one meal. The amount of each component per meal is shown in Table 4.

Example 2

The liquid diet for blend 1 prepared by the method of Preparation Example 1 in an amount of 300 g, and the liquid diet for blend 4 prepared by the method of Preparation Example 2 in an amount of 1,200 g were mixed to obtain a concentrated liquid diet. Packaging and sterilization were carried out similarly to Example 1. The amount of each component per meal is shown in Table 4.

Example 3

A concentrated liquid diet was obtained from only the liquid diet for blend 4 prepared by the method of Preparation Example 2. Packaging and sterilization were carried out similarly to Example 1. The amount of each component per meal is shown in Table 4.

Example 4

The liquid diet for blend 2 prepared by the method of Preparation Example 1 in an amount of 600 g, and the liquid diet for blend 5 prepared by the method of Preparation Example 2 in an amount of 900 g were mixed to obtain a concentrated liquid diet. Packaging and sterilization were carried out similarly to Example 1. The amount of each component per meal is shown in Table 4.

Example 5

The liquid diet for blend 2 prepared by the method of Preparation Example 1 in an amount of 300 g, and the liquid diet for blend 5 prepared by the method of Preparation Example 2 in an amount of 1,200 g were mixed to obtain a concentrated liquid diet. Packaging and sterilization were carried out similarly to Example 1. The amount of each component per meal is shown in Table 4.

Example 6

A concentrated liquid diet was obtained from only the liquid diet for blend 5 prepared by the method of Preparation Example 2. Packaging and sterilization were carried out similarly to Example 1. The amount of each component per meal is shown in Table 4.

Comparative Example 1

The liquid diet for blend 1 prepared by the method of Preparation Example 1 in an amount of 900 g, and the liquid diet for blend 4 prepared by the method of Preparation Example 2 in an amount of 600 g were mixed to obtain a concentrated liquid diet. Packaging and sterilization were carried out similarly to Example 1. The amount of each component per meal is shown in Table 5.

Comparative Example 2

The liquid diet for blend 2 prepared by the method of Preparation Example 1 in an amount of 900 g, and the liquid diet for blend 5 prepared by the method of Preparation Example 2 in an amount of 600 g were mixed to obtain a concentrated liquid diet. Packaging and sterilization were carried out similarly to Example 1. The amount of each component per meal is shown in Table 5.

Comparative Example 3

The liquid diet for blend 3 prepared by the method of Preparation Example 1 in an amount of 900 g, and the liquid diet for blend 6 prepared by the method of Preparation Example 2 in an amount of 600 g were mixed to obtain a concentrated liquid diet. Packaging and sterilization were carried out similarly to Example 1. The amount of each component per meal is shown in Table 5.

Comparative Example 4

The liquid diet for blend 3 prepared by the method of Preparation Example 1 in an amount of 600 g, and the liquid diet for blend 6 prepared by the method of Preparation Example 2 in an amount of 900 g were mixed to obtain a concentrated liquid diet. Packaging and sterilization were carried out similarly to Example 1. The amount of each component per meal is shown in Table 5.

TABLE 4

| Composition of concentrated liquid diet | | | | | | |
|---|---|---|---|---|---|---|
| | Example 1 | Example 2 | Example 3 | Example 4 | Example 5 | Example 6 |
| n-Octanoic Acid:n-Decanoic Acid in Triglyceride | 40:60 | 20:80 | 0:100 | 40:60 | 20:80 | 0:100 |
| Total amount of medium-chain fatty acid having 8 carbon atoms and medium-chain fatty acid having 10 carbon atoms included as constitutive fatty acids of triglyceride (g/100 kcal) | 2.8 | 2.8 | 2.8 | 5.6 | 5.6 | 5.6 |
| Component | Amount ingested (g) per meal | | | | | |
| Triglyceride | 3.00 | 3.00 | 3.00 | 6.00 | 6.00 | 6.00 |
| Casein | 2.00 | 2.00 | 2.00 | 2.00 | 2.00 | 2.00 |
| Whole milk powder | 2.00 | 2.00 | 2.00 | 2.00 | 2.00 | 2.00 |
| White superior soft sugar | 1.00 | 1.00 | 1.00 | 1.00 | 1.00 | 1.00 |
| Dextrin | 14.00 | 14.00 | 14.00 | 7.00 | 7.00 | 7.00 |
| Emulsifying agent | 0.09 | 0.09 | 0.09 | 0.18 | 0.18 | 0.18 |
| Water | 78.00 | 78.00 | 78.00 | 82.00 | 82.00 | 82.00 |
| Total amount | 100.09 | 100.09 | 100.09 | 100.18 | 100.18 | 100.18 |
| Energy (kcal) | 100 | 100 | 100 | 100 | 100 | 100 |

TABLE 5

Composition of concentrated liquid diet

|  | Comparative Example 1 | Comparative Example 2 | Comparative Example 3 | Comparative Example 4 |
|---|---|---|---|---|
| n-Octanoic Acid:n-Decanoic Acid in Triglyceride | 60:40 | 60:40 | 60:40 | 40:60 |
| Total amount of medium-chain fatty acid having 8 carbon atoms and medium-chain fatty acid having 10 carbon atoms included as constitutive fatty acids of triglyceride (g/100 kcal) | 2.8 | 5.5 | 8.3 | 8.3 |

| Component | Amount ingested (g) per meal | | | |
|---|---|---|---|---|
| Triglyceride | 3.00 | 6.00 | 9.00 | 9.00 |
| Casein | 2.00 | 2.00 | 2.00 | 2.00 |
| Whole milk powder | 2.00 | 2.00 | 2.00 | 2.00 |
| White superior soft sugar | 1.00 | 1.00 | 1.00 | 1.00 |
| Dextrin | 14.00 | 7.00 | 0.00 | 0.00 |
| Emulsifying agent | 0.09 | 0.18 | 0.27 | 0.27 |
| Water | 78.00 | 82.00 | 86.00 | 86.00 |
| Total amount | 100.09 | 100.18 | 100.27 | 100.27 |
| Energy (kcal) | 100 | 100 | 100 | 100 |

[Test Method]

Tests were carried out on eighteen healthy adult men and women (20 to 60 years old) who were able to sense discomfort of the upper abdomen such as heavy stomach feeling by ingestion of a test meal in a preliminary test. The test conditions are shown in Table 6.

In each group, the same subject was allowed to ingest the concentrated liquid diets of Comparative Examples and Examples. On the next day of the test day on which one concentrated liquid diet was ingested, the test was not subsequently carried out, and the following test was carried out one or more day after the next day.

On the day before the test, the following items were instructed to follow. (1) Record contents and time and meal time of the dinner; and (2) refrain from drinking alcohol, overeating and overdrinking, and any matter which may lead to strain on the stomach, and avoid from taking something other than water after 21:00 PM.

In addition, on the day of the test, the following items were instructed to follow. (1) Take a standard meal (water and jelly) for breakfast before 07:00 AM, and avoid taking anything other than water thereafter, (2) Fill in a questionnaire in connection with usual state of the stomach before the test, (3) Fill in a questionnaire in connection with occurrence of discomfort and the extent thereof of the abdomen from 15 min to 3 hrs after taking the food at 15 minute intervals, (4) keep a state quiet during the test in terms of both mind and body, and refrain from phone communication, and (5) take fluid ad libitum each with a cup having a volume of about 50 ml, but refrain from intake in a large amount.

TABLE 6

| | test condition | | |
|---|---|---|---|
| Group | Amount of triglyceride ingested | Concentrated liquid diet | Number of subjects |
| 1 | 3 g | Examples 1 to 3, Comparative Example 1 | 6 persons |
| 2 | 6 g | Examples 4 to 6, Comparative Example 2 | 5 persons |
| 3 | 9 g | Comparative Examples 3 and 4 | 7 persons |

The questionnaire in the test included five items of "feeling irritation of the upper abdomen", "feeling sense of distension", "getting nausea", "belching" and "feeling warmth of upper abdomen" to fill in to rate on a 4-point scale of "absent", "slightly present", "present" and "significantly present". These were scored, and individual scores of each item and total score of each item were calculated, and comparison was made. Details of the evaluation score are shown below.

[Evaluation Score]

score 0: absent
score 1: slightly present
score 2: present
score 3: significantly present

TABLE 7

Test for Investigating Discomfort of the Upper Abdomen of Human (triglyceride 3 grams-ingested group)

|  | Concentrated liquid diet | | | |
| --- | --- | --- | --- | --- |
|  | Comparative Example 1 | Example 1 | Example 2 | Example 3 |
| n-Octanoic Acid:n-Decanoic Acid in Triglyceride | 60:40 | 40:60 | 20:80 | 0:100 |
| Total amount of medium-chain fatty acid having 8 carbon atoms and medium-chain fatty acid having 10 carbon atoms included as constitutive fatty acids of triglyceride (g/100 kcal) | 2.8 | 2.8 | 2.8 | 2.8 |
| Evaluation items | Evaluation score | | | |
| Feeling irritation of the upper abdomen | 3.8 ± 5.6 | 5.2 ± 7.0 | 2.8 ± 4.3 | 2.8 ± 4.4** |
| Sensing distension | 8.5 ± 10.7 | 6.3 ± 10.3** | 5.8 ± 8.4** | 4.0 ± 4.8** |
| Getting nausea | 0.5 ± 0.8 | 0.2 ± 0.4** | 1.2 ± 2.4 | 0.5 ± 1.2 |
| Belching | 1.2 ± 1.9 | 0.7 ± 1.2 | 0.3 ± 0.5 | 1.5 ± 2.0 |
| Feeling warmth of upper abdomen | 2.5 ± 3.8 | 1.0 ± 1.3 | 0.5 ± 0.8 | 1.2 ± 1.8 |
| Total score | 16.5 ± 16.2 | 13.3 ± 16.1 | 10.7 ± 12.2 | 10.0 ± 10.1* |

Mean ± SD

**Greater tendency as compared with Comparative Example 1 ($0.1 > P > 0.05$)

*Significantly different as compared with Comparative Example 1 ($P < 0.05$)

TABLE 8

Test for Investigating Discomfort of the Upper Abdomen of Human (triglyceride 6 grams-ingested group)

|  | Concentrated liquid diet | | | |
| --- | --- | --- | --- | --- |
|  | Comparative example 2 | Example 4 | Example 5 | Example 6 |
| n-Octanoic Acid:n-Decanoic Acid in Triglyceride | 60:40 | 40:60 | 20:80 | 0:100 |
| Total amount of medium-chain fatty acid having 8 carbon atoms and medium-chain fatty acid having 10 carbon atoms included as constitutive fatty acids of triglyceride (g/100 kcal) | 5.5 | 5.6 | 5.6 | 5.6 |
| Evaluation items | Evaluation score | | | |
| Feeling irritation of the upper abdomen | 3.2 ± 5.2 | 2.8 ± 3.8 | 2.0 ± 2.8 | 0.2 ± 0.4 |
| Sensing distension | 3.0 ± 3.1 | 2.4 ± 4.8 | 0.6 ± 0.9** | 0.0 ± 0.0* |
| Getting nausea | 0.0 ± 0.0 | 0.0 ± 0.0 | 0.0 ± 0.0 | 0.0 ± 0.0 |
| Belching | 1.8 ± 2.9 | 1.2 ± 2.7* | 0.0 ± 0.0* | 1.0 ± 2.2* |
| Feeling warmth of upper abdomen | 3.4 ± 2.4 | 2.2 ± 2.7** | 1.4 ± 1.9** | 1.8 ± 2.5 |
| Total score | 11.4 ± 10.9 | 8.6 ± 8.9 | 4.0 ± 3.4** | 3.0 ± 4.5* |

Mean ± SD

**Greater tendency as compared with Comparative Example 2 ($0.1 > P > 0.05$)

*Significantly different as compared with Comparative Example 2 ($P < 0.05$)

TABLE 9

Test for Investigating Discomfort of the Upper Abdomen of Human (triglyceride 9 grams-ingested group)

| | Concentrated liquid diet | |
|---|---|---|
| | Comparative example 3 | Comparative example 4 |
| n-Octanoic Acid:n-Decanoic Acid in Triglyceride | 60:40 | 40:60 |
| Total amount of medium-chain fatty acid having 8 carbon atoms and medium-chain fatty acid having 10 carbon atoms included as constitutive fatty acids of triglyceride (g/100 kcal) | 8.3 | 8.3 |
| Evaluation items | Evaluation score | |
| Feeling irritation of the upper abdomen | 3.9 ± 6.3 | 5.1 ± 7.6 |
| Sensing distension | 5.3 ± 7.2 | 4.6 ± 6.1 |
| Getting nausea | 0.4 ± 0.8 | 3.1 ± 4.6** |
| Belching | 1.7 ± 1.5 | 1.7 ± 1.7 |
| Feeling warmth of upper abdomen | 2.7 ± 4.3 | 3.6 ± 4.3 |
| Total score | 14.1 ± 10.8 | 18.1 ± 15.0 |

Mean ± SD
**Greater tendency as compared with Comparative Example 3 (0.1 > P > 0.05)

The results are summarized for each amount of the triglyceride ingested. The results of 3 grams-ingested group (total amount of the medium-chain fatty acid having 8 carbon atoms and the medium-chain fatty acid having 10 carbon atoms ingested: 2.8 g included as the constitutive fatty acids of the triglyceride) are shown in Table 7; the results of 6 grams-ingested group (total amount of the medium-chain fatty acid having 8 carbon atoms and the medium-chain fatty acid having 10 carbon atoms ingested: 5.5 or 5.6 g included as the constitutive fatty acids of the triglyceride) are shown in Table 8; the results of 9 grams-ingested group (total amount of the medium-chain fatty acid having 8 carbon atoms and the medium-chain fatty acid having 10 carbon atoms ingested: 8.3 g included as the constitutive fatty acids of the triglyceride) are shown in Table 9.

In the 3 grams-ingested group, lower values tended to be found for Example 3 as compared with Comparative Example 1 in connection with the item "feeling irritation of the upper abdomen". Also, in connection with the "feeling sense of distension", lower values tended to be found for Examples 1, 2 and 3. In addition, significantly lower values were found for Example 6 in connection with "total score" of each item.

In the 6 grams-ingested group, lower values tended to be found for Example 5 as compared with Comparative Example 2 in connection with "feeling sense of distension", and significantly lower values were found for Example 6. In addition, significantly lower values were found for Examples 4, 5 and 6 in connection with "belching". Moreover, lower values tended to be found for Examples 4 and 5 in connection with "feeling warmth of upper abdomen". Additionally, in connection with "total score" of each item, lower values tended to be found for Example 5, and significantly lower values were found for Example 6.

In the 9 grams-ingested group, higher values tended to be found for Comparative Example 4 as compared with Comparative Example 3 in connection with "getting nausea"; however, a significant difference was not found in connection with any item but almost the same results were revealed.

Investigation of the relationship between the amount of the triglyceride ingested, and the influence on the perception of upper abdominal sensations proves that in connection with "getting nausea", lower values tended to be found for Examples 1 and 4 as compared with Comparative Example 4, whereas in connection with "feeling warmth of upper abdomen", significantly lower values were found for Example 1, and lower values tended to be found for Example 4 in connection with "total score".

From the foregoing results, it was verified that with respect of fatty acids constituting a triglyceride, when the rate of the medium-chain fatty acid having 10 carbon atoms is higher than the rate of the medium-chain fatty acid having 8 carbon atoms, discomfort of the upper abdomen decreased. In addition, it was also verified that discomfort of the upper abdomen increased depending on the amount of the triglyceride ingested.

Production Example 3

Method for Producing Mixed Medium-Chain Triglyceride

Glycerol tri-n-octanoate produced by a similar method to Production Example 1 in an amount of 2 kg, and glycerol tri-n-decanoate produced by a similar method to Production Example 2 in an amount of 8 kg were mixed to obtain 10 kg of a mixed medium-chain triglyceride (in the total mass of the medium-chain fatty acid having 8 carbon atoms and the medium-chain fatty acid having 10 carbon atoms included as constitutive fatty acids of the triglyceride, the rate of the medium-chain fatty acid having 10 carbon atoms being 80% by mass, and the rate of the medium-chain fatty acid having 8 carbon atoms being 20% by mass).

[Preparation of Concentrated Liquid Diet]

Example 7

A retort concentrated liquid diet of coffee flavor blended as shown in Table 10 was produced. Specifically, to 7.047 kg of water at 70° C. were added 1.84 kg of reduced starch syrup and 0.31 kg of modified starch, and mixed with a disperser to permit dissolution. To the mixture was gradually added 0.48 kg of the mixed medium-chain triglyceride produced by the method of Production Example 3 while stirring with a homomixer, followed by adding 0.3 kg of a coffee extract, 0.02 kg of a coffee flavor and 0.003 kg of sodium bicarbonate to obtain 10 kg of a concentrated liquid diet of coffee flavor. After each 125 g (for one meal) of thus obtained concentrated liquid diet of coffee flavor was packed into aluminum laminated pouches and sealed, a retort treatment was carried out at 120° C. for 20 min, and cooled to produce a retort concentrated liquid diet of coffee flavor. It should be noted that a total amount of a medium-chain fatty acid having 8 carbon atoms and a medium-chain fatty acid having 10 carbon atoms included as constitutive fatty acids of the triglyceride per 100 kcal of the energy of thus produced retort concentrated liquid diet of coffee flavor was 3.5 (5.6/159×100=3.52) g, and the amount of the triglyceride per 100 kcal of the energy of the retort concentrated liquid diet was 3.8 g.

TABLE 10

Composition of retort concentrated liquid diet of coffee flavor

| Component | Amount ingested (g) per meal | Blend (% by mass) |
|---|---|---|
| Reduced starch syrup | 23.0 | 18.4 |
| Modified starch | 3.9 | 3.1 |
| Mixed medium-chain triglyceride | 6.0 | 4.8 |
| Coffee extract | 3.8 | 3.0 |
| Coffee flavor | 0.2 | 0.2 |
| Sodium bicarbonate | 0.04 | 0.03 |
| Water | 88 | 70.47 |
| Total | 125 | 100.0 |
| Energy (kcal) | 159 | — |

Example 8

A retort concentrated liquid diet of tea flavor blended as shown in Table 11 was produced.

Specifically, to 7.19 kg of water at 70° C. were added 1.84 kg of reduced starch syrup and 0.31 kg of modified starch, and mixed with a disperser to permit dissolution. To the mixture was gradually added 0.48 kg of the mixed medium-chain triglyceride produced by the method of Production Example 3 while stirring with a homomixer, followed by adding 0.16 kg of a tea extract and 0.02 kg of a tea flavor to obtain 10 kg of a concentrated liquid diet of tea flavor. After each 125 g (for one meal) of thus obtained concentrated liquid diet of tea flavor was packed into aluminum laminated pouches and sealed, a retort treatment was carried out at 120° C. for 20 min, and cooled to produce a retort concentrated liquid diet of tea flavor. It should be noted that a total amount of a medium-chain fatty acid having 8 carbon atoms and a medium-chain fatty acid having 10 carbon atoms included as constitutive fatty acids of the triglyceride per 100 kcal of the energy of thus produced retort concentrated liquid diet of tea flavor was 3.5 (5.6/159×100=3.52) g, and the amount of the triglyceride per 100 kcal of the energy of the retort concentrated liquid diet was 3.8 g.

TABLE 11

Composition of retort concentrated liquid diet of tea flavor

| Component | Amount ingested (g) per meal | Blend (% by mass) |
|---|---|---|
| Reduced starch syrup | 23.0 | 18.4 |
| Modified starch | 3.9 | 3.1 |
| Mixed medium-chain triglyceride | 6.0 | 4.8 |
| Tea extract | 2.0 | 1.6 |
| Tea flavor | 0.2 | 0.2 |
| Water | 90 | 71.9 |
| Total | 125 | 100 |
| Energy (kcal) | 159 | — |

Example 9

Using the mixed medium-chain triglyceride produced by the method of Production Example 3, pumpkin, dextrin, modified starch, water and seasonings as basic ingredients, a pumpkin soup having low salt and protein contents and high energy (concentrated liquid diet) was obtained that had the amount of the mixed medium-chain triglyceride, a protein content, a salt content, and a potassium content of 6 g, no greater than 0.9 g, no greater than 0.4 g, and no greater than 100 mg, respectively, and had an energy per meal of 161 kcal. Each 142 g of thus obtained pumpkin soup per meal was packed into an aluminum laminated pouch for each meal and sealed, and subjected to a retort treatment to produce a retort pumpkin soup (retort concentrated liquid diet). It should be noted that a total amount of a medium-chain fatty acid having 8 carbon atoms and a medium-chain fatty acid having 10 carbon atoms included as constitutive fatty acids of the triglyceride per 100 kcal of the energy of thus produced retort pumpkin soup was 3.5 (5.6/161×100=3.47) g, and the amount of the triglyceride per 100 kcal of the energy of the retort concentrated liquid diet was 3.7 g.

Example 10

Using the mixed medium-chain triglyceride produced by the method of Production Example 3, corn, onion, dextrin, modified starch, water and seasonings as basic ingredients, a corn soup having low salt and protein contents and high energy (concentrated liquid diet) was obtained that had the amount of the mixed medium-chain triglyceride, a protein content, a salt content, and a potassium content of 6 g, no greater than 0.9 g, no greater than 0.4 g, and no greater than 100 mg, respectively, and had an energy per meal of 166 kcal. Each 141 g of thus obtained corn soup per meal was packed into an aluminum laminated pouch for each meal and sealed, and subjected to a retort treatment to produce a retort corn soup (retort concentrated liquid diet). It should be noted that a total amount of a medium-chain fatty acid having 8 carbon atoms and a medium-chain fatty acid having 10 carbon atoms included as constitutive fatty acids of the triglyceride per 100 kcal of the energy of thus produced retort corn soup was 3.4 (5.6/166×100=3.37) g, and the amount of the triglyceride per 100 kcal of the energy of the retort concentrated liquid diet was 3.6 g.

A number of implementations have been described. Nevertheless, it will be understood that various modifications may be made without departing from the spirit and scope of the disclosure. Accordingly, other implementations are within the scope of the following claims.

The invention claimed is:

1. A concentrated liquid diet comprising medium-chain fatty acid triglycerides, each of which comprises at least one of a medium-chain fatty acid having 8 carbon atoms and a medium-chain fatty acid having 10 carbon atoms as constitutive fatty acids of the triglyceride,
   wherein the total amount of the medium-chain fatty acid having 8 carbon atoms and the medium-chain fatty acid having 10 carbon atoms as constitutive fatty acids of the triglyceride is 2.5 to 8.0 g per 100 kcal of the energy of the concentrated liquid diet,
   the total amount of the medium-chain fatty acid having 10 carbon atoms is 60% to 100% of the total mass of the medium-chain fatty acids in the concentrated liquid diet; and
   the total amount of the medium-chain fatty acid having 8 carbon atoms is 5% to 40% of the total mass of the medium-chain fatty acids in the concentrated liquid diet.

2. The concentrated liquid diet of claim 1, wherein the total amount of the medium-chain fatty acid having 8 carbon atoms and the medium-chain fatty acid having 10 carbon atoms as constitutive fatty acids of the triglyceride is 2.5 to 6.0 g per 100 kcal of the energy of the concentrated liquid diet.

3. The concentrated liquid diet of claim 1, wherein the total amount of the medium-chain fatty acid having 10 carbon atoms is 75% or more and 100% or less of the total mass of the medium-chain fatty acids in the concentrated liquid diet.

4. The concentrated liquid diet of claim 1, wherein the concentrated liquid diet comprises the triglyceride in an amount of 2.6 to 10 g per 100 kcal of the energy of the concentrated liquid diet.

5. The concentrated liquid diet of claim 1, wherein the concentrated liquid diet is in the form of a soup, enteral formula or parenteral formula.

6. The concentrated liquid diet of claim 1, further comprising an oil selected from the group consisting of soybean oil, rapeseed oil, sesame oil, palm oil, palm kernel oil, coconut oil, and fish oil, or any combination thereof.

7. The concentrated liquid diet of claim 1, further comprising
an oil selected from the group consisting of soybean oil, rapeseed oil, sesame oil, palm oil, palm kernel oil, coconut oil, and fish oil, or any combination thereof; and
one or more components selected from the group consisting of nutritional vitamins, nutritional minerals, emulsifying agents, milk proteins, soybean proteins, dextrin, and a combination thereof.

8. The concentrated liquid diet of claim 1, wherein the concentrated liquid diet has been sterilized prior to administration to the human using a retort sterilization process.

9. A concentrated liquid diet comprising
medium-chain fatty acid triglycerides, each of which comprises at least one of a medium-chain fatty acid having 8 carbon atoms and a medium-chain fatty acid having 10 carbon atoms as constitutive fatty acids of the triglyceride, and
one or more components selected from the group consisting of nutritional vitamins, nutritional minerals, emulsifying agents, milk proteins, soybean proteins, dextrin, and a combination thereof,
wherein the total amount of the medium-chain fatty acid having 8 carbon atoms and the medium-chain fatty acid having 10 carbon atoms as constitutive fatty acids of the triglyceride is 2.5 to 8.0 g per 100 kcal of the energy of the concentrated liquid diet,
the total amount of the medium-chain fatty acid having 10 carbon atoms is 60% to 100% of the total mass of the medium-chain fatty acids in the concentrated liquid diet; and
the total amount of the medium-chain fatty acid having 8 carbon atoms is 5% to 40% of the total mass of the medium-chain fatty acids in the concentrated liquid diet.

* * * * *